United States Patent
Lashinski et al.

(10) Patent No.: US 6,319,275 B1
(45) Date of Patent: Nov. 20, 2001

(54) ENDOLUMENAL PROSTHESIS DELIVERY ASSEMBLY AND METHOD OF USE

(75) Inventors: Robert D. Lashinski, Sebastopol; Dennis L. Brooks, Windsor; Vance E. Swanson, Santa Rosa, all of CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/287,309

(22) Filed: Apr. 7, 1999

(51) Int. Cl.[7] ........................................................ A61F 2/06
(52) U.S. Cl. ........................................... 623/1.11; 606/108
(58) Field of Search ..................................... 606/108, 194, 606/192; 604/96, 101, 102; 623/1.11

(56) References Cited

U.S. PATENT DOCUMENTS

| | | |
|---|---|---|
| 4,580,568 | 4/1986 | Gianturco . |
| 4,733,665 | 3/1988 | Palmaz . |
| 4,739,762 | 4/1988 | Palmaz . |
| 4,776,337 | 10/1988 | Palmaz . |
| 4,795,458 | 1/1989 | Regan . |
| 4,830,003 | 5/1989 | Wolff et al. . |
| 4,846,174 | 7/1989 | Willard et al. . |
| 4,913,141 | 4/1990 | Hillstead . |
| 4,969,458 | 11/1990 | Wiktor . |
| 5,019,090 | 5/1991 | Pinchuk . |
| 5,222,969 | 6/1993 | Gillis . |
| 5,261,878 | 11/1993 | Galindo . |
| 5,290,295 | * 3/1994 | Querals et al. ........................ 606/108 |
| 5,292,331 | 3/1994 | Boneau . |
| 5,322,501 | 6/1994 | Mahmud-Durrani . |
| 5,439,446 | 8/1995 | Barry . |
| 5,520,645 | 5/1996 | Imran et al. . |
| 5,571,172 | 11/1996 | Chin . |
| 5,628,754 | 5/1997 | Shevlin et al. . |
| 5,628,755 | 5/1997 | Heller et al. . |
| 5,632,760 | 5/1997 | Sheiban et al. . |
| 5,639,274 | 6/1997 | Fischell et al. . |
| 5,666,969 | 9/1997 | Urick . |
| 5,667,522 | 9/1997 | Flomenblit et al. . |
| 6,013,085 | * 1/2000 | Howard ................................ 606/108 |
| B1 4,733,665 | 1/1994 | Palmaz . |

FOREIGN PATENT DOCUMENTS

| | | |
|---|---|---|
| 195 26 784 A1 | 1/1997 | (DE) . |
| 0 533 511 A1 | 3/1993 | (EP) . |
| 0 747 088 A1 | 12/1996 | (EP) . |

* cited by examiner

*Primary Examiner*—Kevin Truong

(57) ABSTRACT

An endolumenal prosthesis delivery assembly includes an endolumenal prosthesis which is delivered to a desired location within a body lumen by used of first and second delivery members. The first delivery member has a prosthesis coupler that is adapted to removeably engage the prosthesis during delivery to the desired location and to release the prosthesis and implant it at the desired location. The second delivery member has an anchor on its distal end portion which is adapted to secure the second delivery member within the body lumen distally of the desired location for stenting. Once the second delivery member is anchored, the first delivery member is slideably advanced over the second delivery member until the prosthesis is positioned at the desired location. The anchor along the second delivery member according to this assembly is either an expandable member, such as a balloon, or is otherwise adapted to engage the body lumen wall, such as by use of suction or other mechanical means. An expansion member on the first delivery member, such as provided at the prosthesis coupler, expands the prosthesis to engage the body lumen wall.

3 Claims, 10 Drawing Sheets

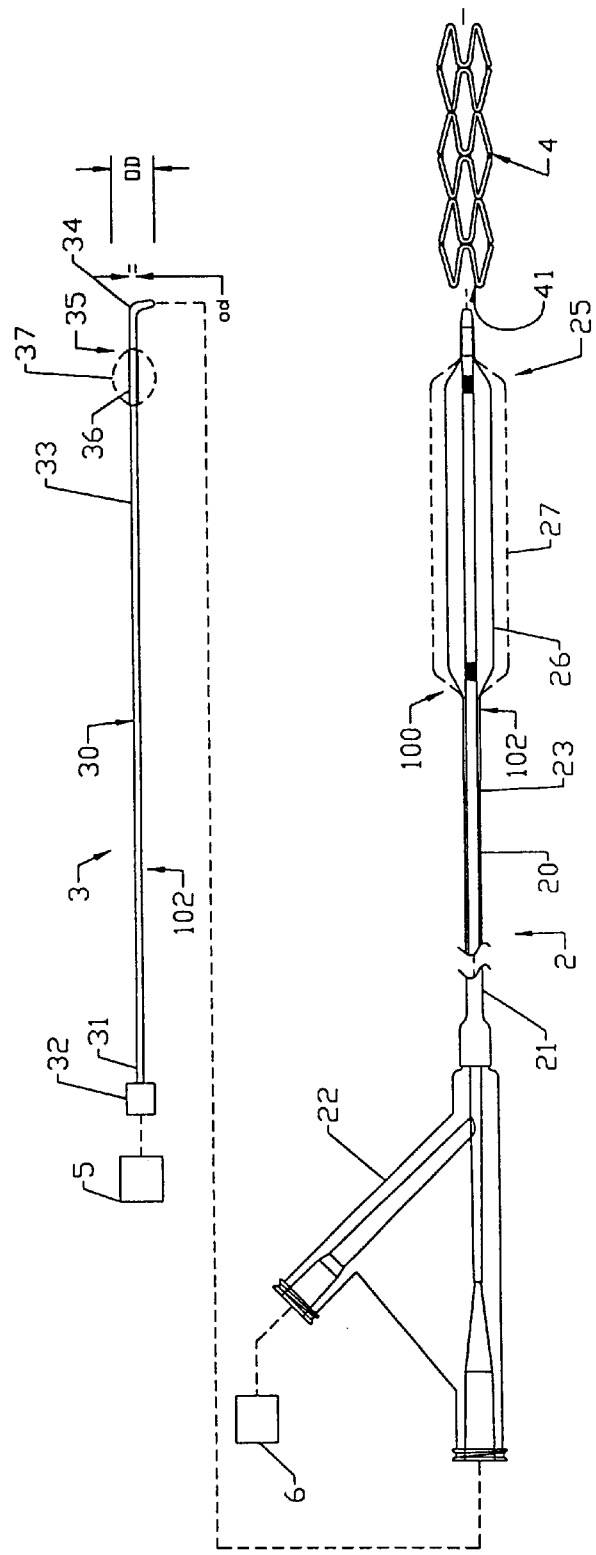
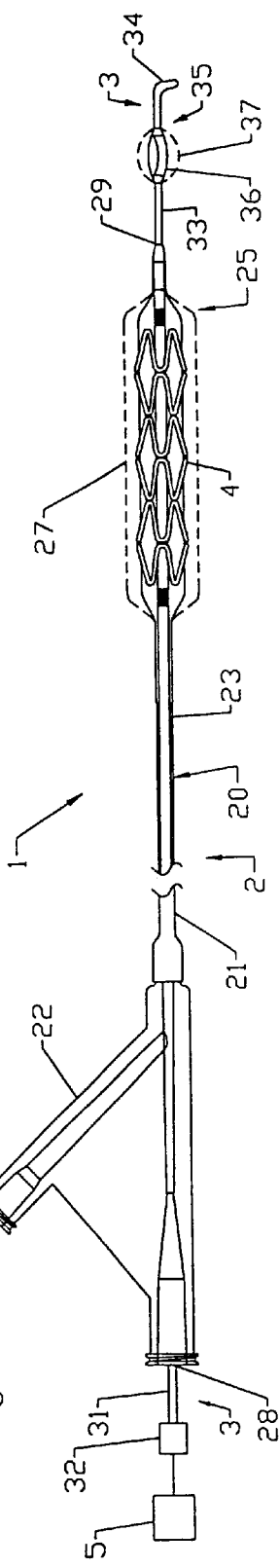
FIGURE 1A
FIGURE 1B

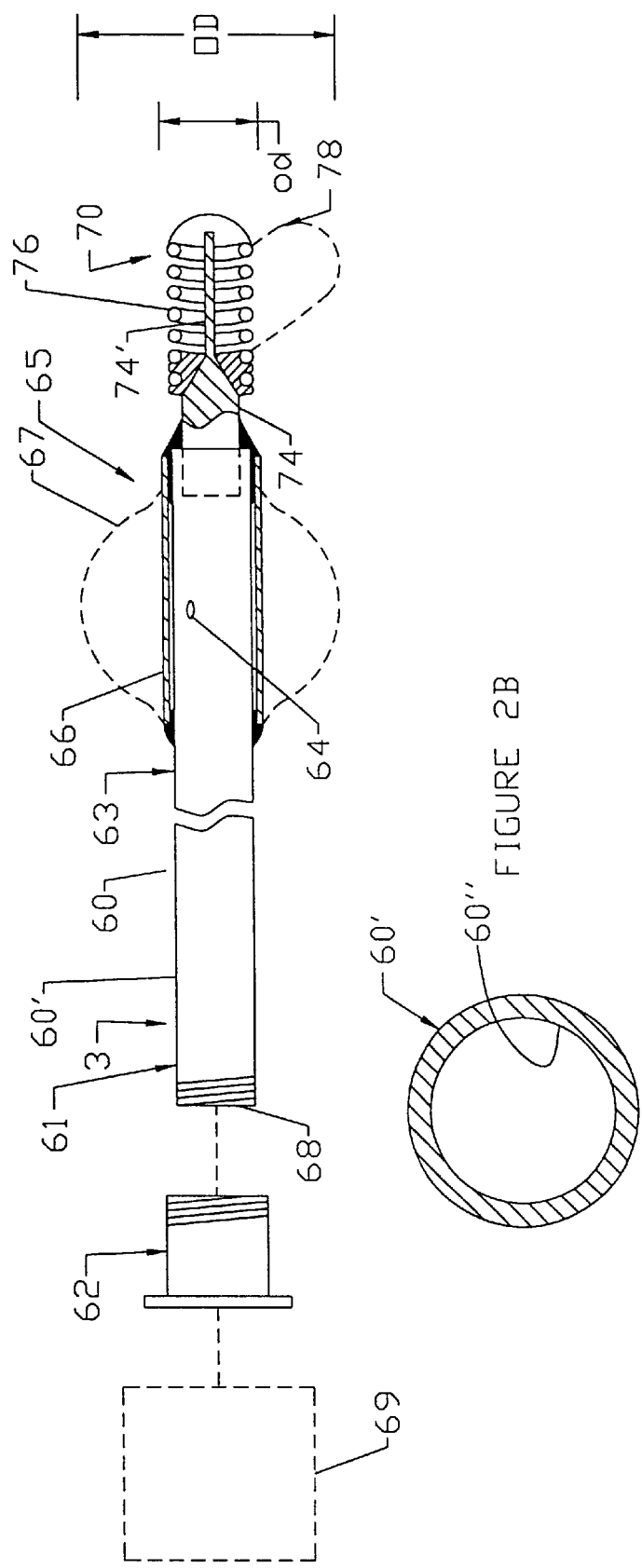

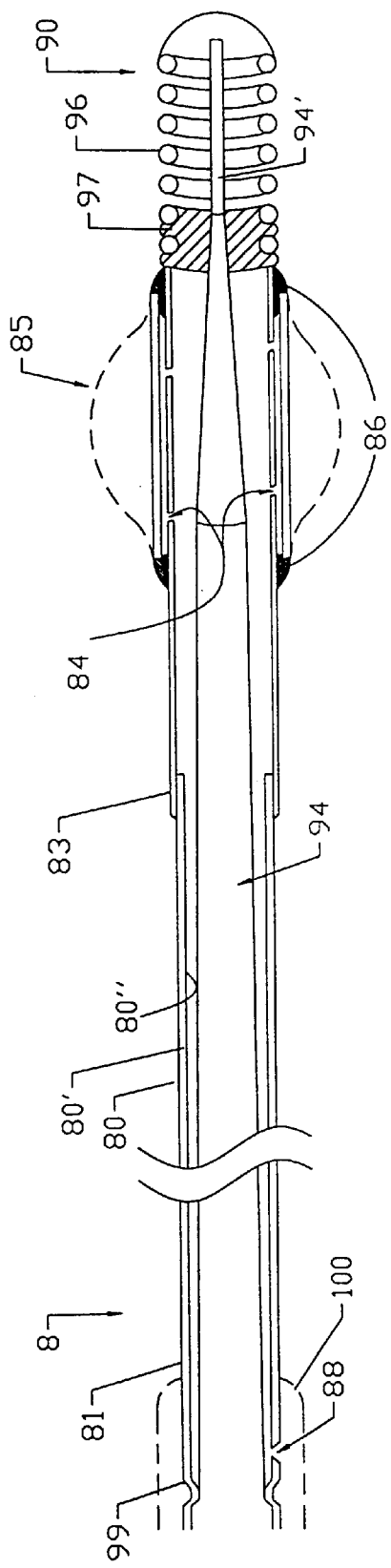
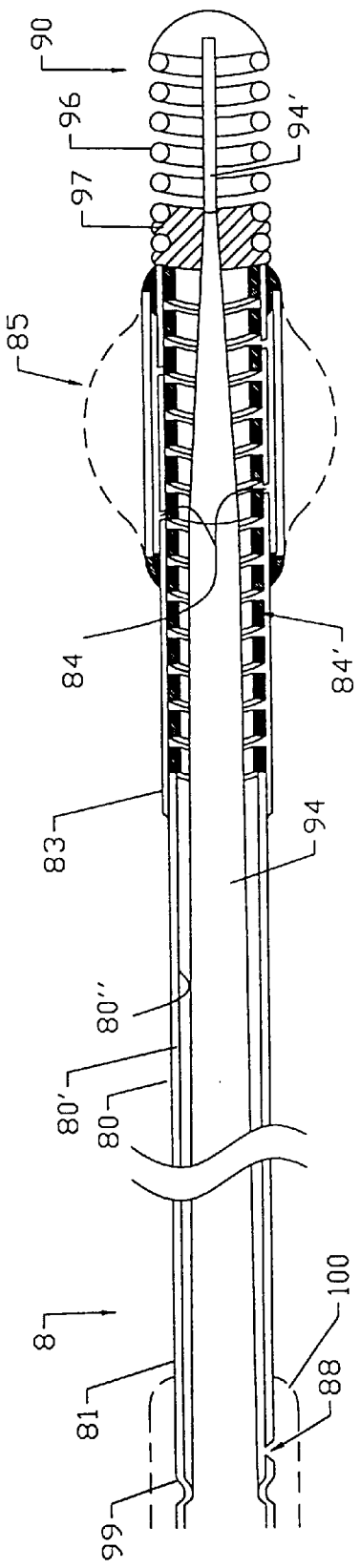
FIGURE 3A
FIGURE 3B

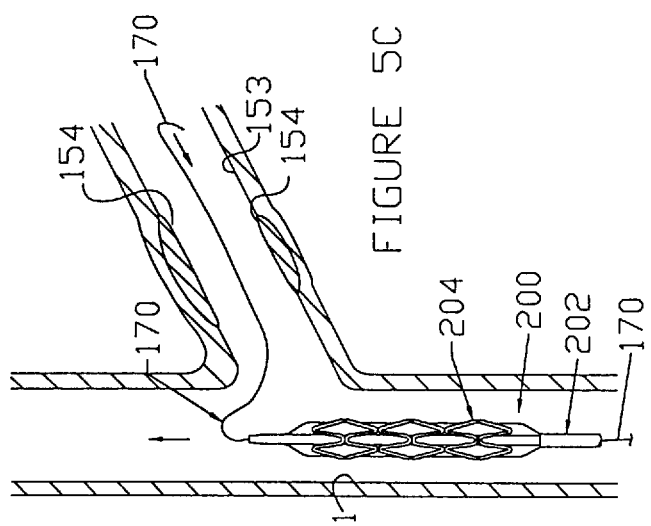
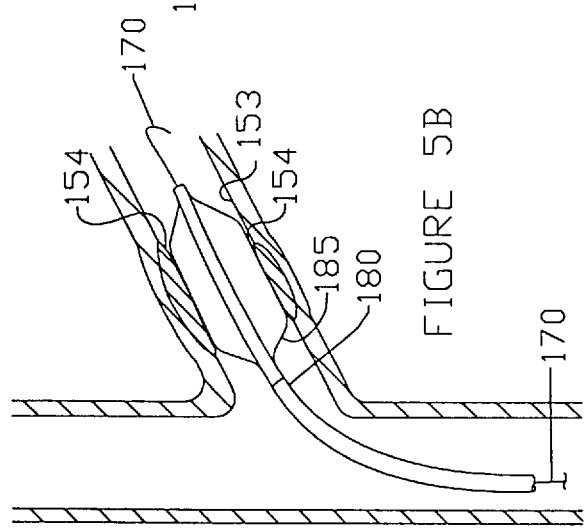
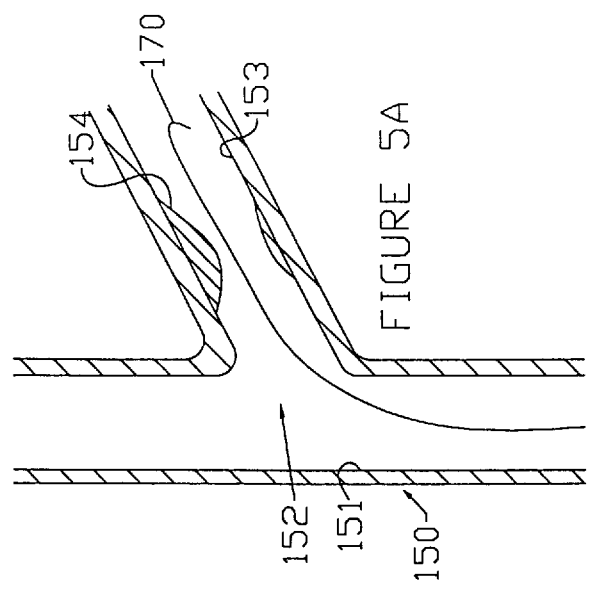

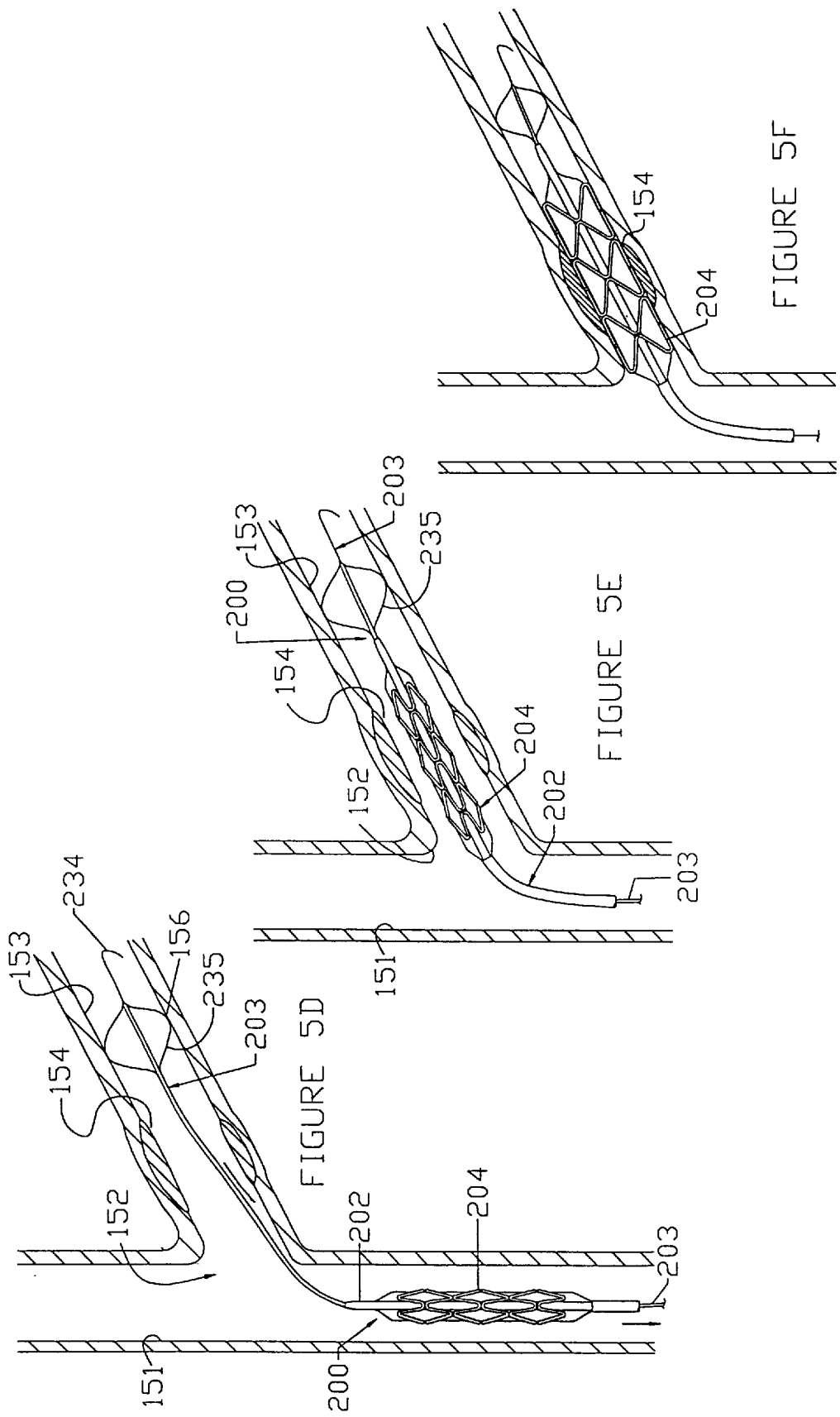

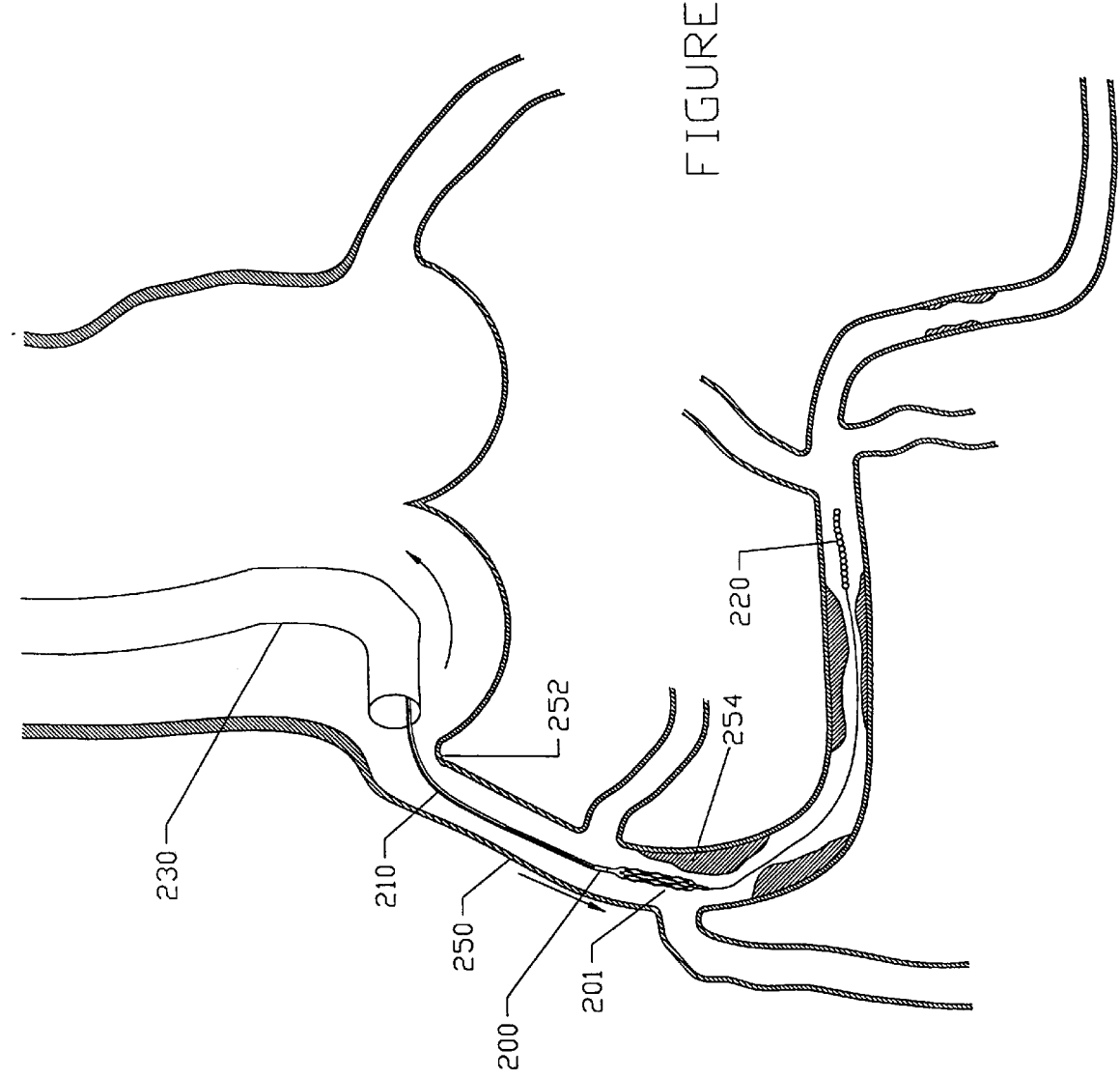

ENDOLUMENAL PROSTHESIS DELIVERY ASSEMBLY AND METHOD OF USE

FIELD OF THE INVENTION

The present invention is a surgical device assembly and method. More particularly, it is an endolumenal prosthesis assembly and method for implanting an endolumenal prosthesis within a body lumen. Still more particularly, the invention is an endolumenal prosthesis delivery assembly with an endolumenal prosthesis releasably coupled to a first delivery member that tracks over a second delivery member which has an anchor that secures the second delivery member within the body lumen distally of the desired location for delivering the prosthesis.

BACKGROUND

A wide range of medical treatments have been previously developed using "endolumenal prostheses," which terms are herein intended to mean medical devices that are adapted to be implanted within a body lumen. Examples of lumens in which endolumenal prostheses may be implanted include, without limitation: blood vessels, including arteries and veins, and such as for example those located within the coronary, mesentery, peripheral, or cerebral vasculature; the gastrointestinal tract; biliary ducts; the urethra; and fallopian tubes.

Various different types of endolumenal prosthesis have also been developed, each providing a uniquely beneficial structure intended to mechanically couple to the specifically targeted lumenal wall. For example, various stents, grafts, and combination stent-graft prostheses have been previously disclosed for implantation within body lumens in order to provide artificial radial support to the lumenal wall tissue while maintaining lumenal patency through the supported region. One more frequently disclosed arterial "stenting" procedure involves implanting a stent in an artery in order to provide radial support to the vessel to thereby prevent abrupt closure subsequent to recanalization of stenosed regions of the artery, such as by balloon angioplasty or atherectomy (mechanical dilation of stenosed vessel by radial balloon expansion or by direct removal of stenotic plaque, respectively).

Conventional Stent Designs

Stents are designed to provide radial support to the vessel wall and also forms a prosthesis passageway or stent lumen extending centrally through the stent in order to provide a conduit for flow through the stented region. Moreover, a wide variety of stent designs have been previously disclosed that differ in the aspect of their structural design. In general, most of these various stent structures include a network of integrated support members having a geometry such that the networked design defines a longitudinal passageway. The structural integrity of the integrated support members provides radial rigidity against physiological collapsible forces at the vessel wall, whereas the longitudinal passageway through the prosthesis allows for flow through the stented region.

Various examples of previously disclosed stent structures include, without limitation: wire mesh; coiled wire; slotted tubes; and connected rings. More detailed examples of these types of stents are also variously disclosed in the following references: U.S. Pat. No. 4,580,568 issued to Gianturco; U.S. Pat. No. 4,655,771 issued to Wallsten; U.S. Pat. No. 4,733,665 issued to Palmaz; U.S. Pat. No. 4,739,762 issued to Palmaz; U.S. Pat. No. 4,776,337 issued to Palmaz; U.S. Pat. No. 4,830,003 issued to Wolff et al.; U.S. Pat. No. 5,571,172 issued to Chin; U.S. Pat. No. 4,913,141 to Hillstead; U.S. Pat. No. 4,969,458 issued to Wiktor; U.S. Pat. No. 5,019,090 issued to Pinchuk; and U.S. Pat. No. 5,292,331 issued to Boneau; U.S. Pat. No. 5,817,152 issued to Birdsall. The disclosures of these references are herein incorporated in their entirety by reference thereto.

Conventional Stent Delivery Assemblies & Methods

Various stent delivery assemblies and methods have also been disclosed which are adapted to deliver particular stents within desired locations of specific body lumens or lumens and to thereafter implant the stents at their respectively desired locations. In general, stents are adapted to be delivered to the desired location by engaging the stent in a radially collapsed condition to a coupler on a delivery member or catheter which is adapted to be delivered to the desired location via known access procedures, such as for example via known translumenal procedures. In a further more detailed example adapted for percutaneous translumenal catheterization procedures, the delivery member is a catheter which is adapted to track over a second delivery member, such as for example a guidewire, which is specifically adapted to subselect a percutaneous translumenal path to the desired location and provide a rail for the first delivery member to follow.

Once delivered and positioned at the desired location for implantation, the stent is then adjusted to a radially expanded condition which is adapted to radially engage the interior surface of the lumenal wall tissue, such as a vessel wall in an arterial stenting procedure. Further to this generally applicable stent delivery method just described, various stent designs have also been disclosed which differ in the aspect of their structure which allows the expansion from the radially collapsed condition to the radially expanded condition. Examples of different stent structures which are adapted according to these varied modes of delivery include, without limitation: "self-expanding" stents, which generally expand under their own force once delivered to the desired stenting site; and "balloon expandable" stents, which generally expand under mechanical strain from an inflating balloon at the stenting site.

Further to the "self-expanding" stent variation just described, one more detailed example of this type of stent is adjustable from the radially collapsed condition to the radially expanded condition by removing a radial constraining member once delivered to the stenting site. This type of self-expanding stent is adapted to recover from an elastically deformed state, when radially confined by the constraining member in the radially collapsed condition, to a resting or recovered state in the radially expanded condition, when radially unconstrained. Further detailed examples of known constraining members for use in delivery systems for such known self-expanding stents include, without limitation, radially confining sheaths, releasable tethers, and other securing devices which are releasably coupled to the stent wall when in the radially collapsed condition. Still further, another more specific example of a previously disclosed "self-expanding" stent is one which is formed from a shape-memory alloy and is adjustable from the radially collapsed condition to the radially expanded condition by heating the stent once delivered to the stenting site, thereby inducing a heat-memory recovery of the material in the stent wall to the radially expanded condition. One drawback of self-expanding stent assemblies is the difficulty of accurate positioning. Specifically, the stent tends to advance or "pop" forward when released. For example, a self-expanding stent assembly utilizing a radially confining sheath will typically include an inner member to hold the stent in position while the outer sheath is removed. However, it has been observed that when the sheath is withdrawn, the stent tends to advance in unpredictable fashion.

Further to the "balloon expandable" stent variation previously described, according to one more detailed example a stent is crimped or otherwise held in the radially collapsed condition over an exterior surface of a balloon on the distal end of a balloon catheter. The balloon catheter is adapted to track over a guidewire to the desired location for stent implantation. Inflating the balloon at the desired location adjusts the stent to the radially expanded condition which is adapted to engage the body lumen or lumen wall. Subsequent deflation of the balloon thereby leaves the stent implanted within the lumen. Further detailed examples of previously known "balloon expandable" stents and related delivery assemblies include, without limitation: assemblies which provide stents "pre-loaded" over a balloon catheter; and assemblies which provide a stent to a user separately from the balloon delivery assembly, allowing the user to crimp the stent onto the balloon immediately prior to delivery in vivo.

Further more specific examples of specific stent designs which are adapted for the various modes of delivery just described above are disclosed variously throughout the following references, the disclosures of which have been previously incorporated by reference thereto: U.S. Pat. No. 4,580,568 issued to Gianturco; U.S. Pat. No. 5,571,172 issued to Chin; U.S. Pat. No. 4,733,665 issued to Palmaz; U.S. Pat. No. 4,739,762 issued to Palmaz; U.S. Pat. No. 4,776,337 issued to Palmaz; U.S. Pat. No. 4,830,003 issued to Wolff et al.; U.S. Pat. No. 4,913,141 issued to Hillstead; U.S. Pat. No. 4,969,458 issued to Wiktor; U.S. Pat. No. 5,019,090 issued to Pinchuk; and U.S. Pat. No. 5,292,331 issued to Boneau; U.S. Pat. No. 5,817,152 issued to Birdsall.

Complex Stent Delivery Systems

In addition to the specifically designed stents and delivery assemblies previously described above, other detailed assemblies and methods have also been disclosed which are specifically designed to overcome the particular anatomic challenges associated with specific stenting procedures.

For example, at least one other stent delivery assembly and method has been disclosed which is specifically adapted for delivering and positioning a stent in the ductus arteriosis. In particular, a double balloon catheter having a first stent delivery balloon located proximal to a second distally located distal end balloon is adapted to be engaged securely within the ductus arteriosis of an infant. After catheter delivery to the delivery site, the distal end balloon is first inflated into a spherical configuration within the ductus arteriosis, then the catheter is withdrawn until the distal balloon abuts the opening. When the abutment is realized, the stent balloon, which carries a stent, is selectively inflated while maintaining the distal end balloon in an inflated condition. This balloon inflation expands and subsequently embeds the stent at the target site in the ductus arteriosis.

In another example, at least one other stent delivery assembly and method is also known which is intended to specifically implant a stent at a desired location in the urethra, and more particularly in order to prevent urethral strictures following a surgical procedure. By reference to one known design according to this application, an elongated cylindrical stent includes a contractible locating member attached at one end and a retrieving string attached at the other end. The contractible member is fastened to the elongated stent body by two flexible strings and is maintained in a radially contracted condition by a cylindrical pusher prior to insertion into the bladder through the narrow urethra lumen. After delivery to the urethra using a pusher along a guidewire, the contractible member is deployed to a radially expandable conformation by removal of the cylindrical pusher, thus lodging the contractible member at the target site.

More detailed examples of stent delivery assemblies and methods of the types just described for use in the ductus arteriosis and urethra are disclosed in the following references: U.S. Pat. No. 5,322,501 issued to Mahmud-Durrani and U.S. Pat. No. 5,261,878 issued to Galindo. The disclosures of these references are herein incorporated in their entirety by reference thereto.

Still further, other stent delivery assemblies have been disclosed which are intended for use in stenting a stenosed region of a vessel in addition to dilating the stenosis, and are herein referred to as "Balloon Dilatation/Stent Delivery" assemblies.

One example of a previously disclosed balloon dilatation/stent delivery assembly comprises an integrated catheter system including a stent catheter and an "over-the-wire" balloon angioplasty catheter. The stent catheter contains a radially expandable stent which is adapted to be held in place over the partially inflated balloon of the balloon catheter upon delivery to the site of lesion. The balloon catheter with the inflatable balloon is positioned at the catheter's distal end which is initially inflated at low pressure to engage the vessel wall and thus dilate the vessel. The stent catheter contains an elongated passageway with a tapered distal end through which the balloon catheter can be slideably moved and a stent which is radially confined within a stent containment cavity which can be adapted to slide over the partially inflated balloon using a guidewire. This same guidewire is used to advance the stent to the site of lesion. The withdrawing of the containment member upon stent delivery to the target site results in a radially expandable deployment of the stent from the containment cavity. The balloon is then inflated radially outward so as to embed the stent within the vessel wall.

Another example of a known balloon dilatation/stent delivery assembly embodies an assembly comprising an a "over-the-wire" balloon angioplasty catheter in combination with a radially expandable stent. The stent delivery guide catheter contains a dilatation catheter with an inflatable balloon which first dilates the stenosis. The balloon is then deflated and withdrawn back into the delivery catheter until it spans the stent and a bladder located within the delivery catheter. The bladder is then inflated by a pressure source thus compressing the stent radially inward to become deposited on the balloon catheter. The dilatation catheter which is now carrying the stent, is once again advanced to the site of lesion in the coronary artery. The balloon is inflated and the stent is implanted into the stenosis.

In another example of a balloon dilatation/stent delivery assembly, a coil shaped stent is initially located proximal to a balloon on a balloon tipped catheter. The balloon tipped catheter is first advanced to the site of the plaque and the balloon is expanded to compress the plaque against the vessel wall. The stent is then advanced along the catheter body onto the balloon of the balloon tipped catheter by a catheter jacket located proximal to the stent. After the balloon is expanded and subsequently withdrawn, the stent remains in situ to reinforce the arterial wall.

According to still a further example of a previously disclosed balloon dilatation/stent delivery assembly, a stent delivery catheter contains two balloons situated near the distal end of the catheter and is introduced into the patient and navigated to the target site by common use of a guidewire. The catheter has bulges located at one end of and within each balloon. A compressed stent is disposed around one balloon and between the bulges. The use of this bulge design allows the stent to be fixed securely about the balloon thus eliminating the need for any stent containment device. The more distally located balloon may be first inflated to dilate the occluded vessel near the stent implantation site.

More specific stent delivery devices and methods according to the above referenced examples may be found variously among the disclosures of the following references: U.S. Pat. No. 5,639,274 issued to Fischell et al.; U.S. Pat. No. 5,222,969 issued to Gillis; U.S. Pat. No. 5,632,760 issued to Sheiban et al.; and U.S. Pat. No. 5,628,754 issued to Shevlin et al. The disclosures of these references are herein incorporated in their entirety by reference thereto.

Notwithstanding the features and intended applications of the various balloon dilatation/stent delivery assemblies just described, many stent delivery assemblies of the "balloon expandable" type are also known to have sufficiently large profiles such that tight stenoses may be difficult to cross initially prior to dilatation stenting. One particular complication which has been observed due to this crossing profile challenge is known as "guide catheter back-out," which is generally described as follows.

Guiding catheters are devices which generally provide a lumenal conduit through which the stent delivery assembly is percutaneously delivered into an ostium of a desired vessel tree in which the stent is to be implanted. In addition, guiding catheters are intended to provide "back-up" support to allow the stent delivery assembly to be pushed through severe bends or against and through a tight lesion. However, a guiding catheter's support can reach its limit upon encountering a sufficiently tight stenosis with the stent assembly. In such a circumstance, the guiding catheter may unseat from the ostium wherein much of the guiding catheter support and concomitant pushability of the stent assembly is lost. In some circumstances, this "back-out" phenomenon may be overcome such as by "deep-seating" the guiding catheter within the ostium, or by replacing the whole system to include a guiding catheter with a different shape or stiffer construction. In other more severe circumstances of tight lesions, however, predilatation of the stenosis with a separate balloon may be required prior to stent delivery.

Accordingly, there remains a need for a stent delivery assembly which effectively prevents guiding catheter back-out when attempting to advance a stent delivery assembly through severe bends or tight lesions.

Another example of a specific stenting procedure which presents particular challenges to conventional stents and stent delivery assemblies includes stenting of bifurcation regions of body lumens. In particular, complications and challenges are known to arise from the use of conventional assemblies and methods in bifurcation regions wherein the desired location for stent implantation is either (a) at or closely adjacent to the bifurcation region; or (b) in a branch vessel distally beyond the bifurcation region.

For example, some bifurcation regions present anatomy which is very difficult to track using conventional "guidewire tracking" delivery assemblies and methods. In one more particular example, a side-branch lumen extends distally from their respective main vessels at drastic "take-off" angles. In such drastic circumstances, even highly trackable and sub-selective guidewires are difficult to position within such takeoffs. However, even in less drastic circumstances where the guidewire is positioned within the side-branch, conventional stents and stent delivery members have been observed to either fail while tracking over the guidewire through such bends or to follow the guidewire only after significant effort.

Moreover, largely due to the presence of the prosthesis in a collapsed and compacted condition during delivery, many stent delivery assemblies are known to be stiffer than many other interventional devices, such as for example when compared with simple balloon angioplasty catheters. Therefore, it has been observed that such stiffness may further complicate the tracking over guidewires through such tortuosities. Accordingly, observed complications in attempting stent delivery in side-branches extending from bifurcations include: prolapsing a guidewire out of the side-branch and into the main lumen while advancing the stent delivery assembly; and guidewire contact or "hang-up" against the nape of the bifurcation which may increase risk of intimal wall damage in severe cases. Also, the complications which may be associated with wall trauma as just described for some bifurcation procedures may also occur in procedures attempting stent delivery beyond severe bends, such as for example beyond bends of greater than thirty degrees, and also for example beyond multiple sequential bends in a given lumen.

In one known method for delivering conventional stents to bifurcations, a side-branch is first stented, after which a second stent is placed within the main vessel which may include a second side-branch. Another known bifurcation stenting method includes first stenting the main vessel and then advancing a second stent through the interior passageway of the main vessel stent and into the side-branch where it is then implanted. These methods, however, are believed to present some incumbent risks, such as for example: sub-optimal results at the side-branch ostium; or "jailing" of the side-branch lumen with a main vessel stent, respectively.

Due to the observed challenges of using conventional stent delivery assemblies and methods for bifurcation stenting procedures, more specifically designed stents and delivery systems have been disclosed which are intended for placement at bifurcation regions. One example of a known "bifurcation" stent and related delivery system includes a Y-shaped stent which is adapted to engage both branches of the bifurcating vessel simultaneously using a corresponding "Y"-shaped delivery assembly with bifurcating balloons. The Y-shaped expandable stent delivery system is intended to avoid damage to the bifurcation region due to sequential positioning of multiple stents. Additional more specific stents, stent delivery devices, and related methods for stenting bifurcations are disclosed in the following references: U.S. Pat. No. 4,994,071 issued to MacGregor and U.S. Pat. No. 5,669,924 issued to Shaknovich. The disclosures of these references are herein incorporated in their entirety by reference thereto.

There is still a need for an endolumenal prosthesis delivery assembly and method for safely and effectively positioning an endolumenal prosthesis within a desired location in a body lumen that is located distally of a severely tortuous bend in the lumen.

There is also still a need for an endolumenal prosthesis delivery assembly and method for safely and efficiently implanting an endolumenal prosthesis within a side-branch lumen extending at a significant angle from a bifurcation region of a vessel.

None of the cited references discloses an endolumenal prosthesis delivery assembly and method for delivering an endolumenal prosthesis within a desired location in a body lumen by anchoring one delivery member within a region of the body lumen distally of the desired location so that another delivery member releasably coupled to the endolumenal prosthesis may slideably engage and track over the first delivery member until the prosthesis is positioned at the desired location.

Nor do the cited references disclose an endolumenal prosthesis delivery assembly with an anchor on a delivery member which is adapted to prevent guiding catheter back-out during delivery of the endolumenal prosthesis with another delivery member to the desired location for implantation.

Moreover, none of the cited references disclose an endolumenal prosthesis delivery assembly with an anchor on a delivery member which is adapted to more precisely and reliably position a self-expanding stent.

SUMMARY OF THE INVENTION

The present invention is an endolumenal prosthesis delivery assembly and method for implanting an endolumenal prosthesis within a body lumen in a mammalian body. This assembly and method are believed to be particularly well suited for delivering an endolumenal prosthesis to a desired location for implantation which is located beyond a tortuous in vivo delivery path, such as in a location along a branch vessel beyond a bifurcation region or otherwise along a lumen which is beyond a significant bend or bends. In addition, the assembly and method are further believed to prevent guiding catheter back-out during delivery of the stent delivery assembly through such resistive anatomy. Moreover, the assembly and method are also believed to enable more accurate and reliable placement of a self-expanding stent.

One mode of the present invention is an endolumenal prosthesis delivery assembly that includes an endolumenal prosthesis and first and second coordinating delivery members. The endolumenal prosthesis is a device which is adapted to be implanted within the body lumen. The first delivery member has a proximal end portion and a distal end portion that further includes a prosthesis coupler which is adapted to releasably engage the endolumenal prosthesis. The second delivery member also has a proximal end portion and a distal end portion, and further includes an anchor which is located along its distal end portion. The anchor is adapted to secure the distal end portion of the second delivery member within the body lumen. Further to this mode, the distal end portion of the first delivery member is adapted to slideably engage and track along the distal end portion of the second delivery member such that the endolumenal prosthesis when engaged to the prosthesis coupler may be positioned along the distal end portion of the second delivery member proximally of the anchor.

In one aspect of the endolumenal prosthesis delivery assembly mode of the invention, the anchor is adjustable from a first position, which is adapted to be delivered within the body lumen, to a second position, which is adapted to be secured within the body lumen. In one variation of this aspect, the anchor includes an expandable member which is adjustable with an expansion member from the first position to the second position. Further to this variation, the first position is characterized by a radially collapsed condition that is adapted to be delivered within the body lumen, and the second position is characterized by a radially expanded condition that is adapted to radially engage the body lumen wall to thereby secure the anchor within the body lumen. In still a further variation, the expandable member is an inflatable balloon, and in a further aspect of this variation the balloon is designed to have a compliance which exhibits at least a two-hundred percent elastic expansion when pressurized by a pressurizeable fluid source to a pressure of approximately three to five atmospheres. In again another variation, the expandable member is an expandable cage or basket which mechanically adjusts to the radially expanded condition for anchoring within a vessel lumen.

In another aspect of the endolumenal prosthesis delivery assembly mode of the invention, the second delivery member is a guidewire with a radiopaque distal tip located distally of the anchor and which is steerable within the body lumen by torquing the proximal end portion of the second delivery member. In one variation of this aspect, the anchor is an inflatable balloon and the second delivery member provides an inflation lumen which is formed at least in part by a tubular member which is also torquable and torsionally coupled to the radiopaque distal tip.

In another aspect of the endolumenal prosthesis delivery assembly mode of the invention, the first delivery member includes a lumen which extends between a distal port located distally of the prosthesis and a proximal port located proximally of the prosthesis. The lumen according to this aspect is adapted to slideably engage and track over the distal end portion of the second delivery member at least proximally of the anchor.

In one further variation of this "tracking lumen" aspect of the first delivery member, the anchor on the second delivery member is adjustable from a first position, which is adapted to slideably engage the lumen through the proximal port and to advance distally of the distal port to be delivered within the body lumen, to a second position, which is adapted to be secured within the body lumen.

In another variation of the "tracking lumen" aspect of the first delivery member, the lumen of the first delivery member has an inner diameter which is smaller than the outer profile of the anchor in the first position. According to this variation, the distal end portion of the second delivery member is adapted to slideably engage the lumen by backloading the second delivery member's proximal end through the distal port, proximally through the lumen, and out of the proximal port. Further to this variation, the first delivery member's distal end portion is adapted to advance and track over the distal end portion of the second delivery member proximal of the anchor.

In still a further more detailed design according to the "backloading" variation just described, the anchor is an inflatable balloon. The second delivery member includes an inflation lumen coupled to the balloon and also a removeable coupler which is adapted to removably engage the second delivery member's proximal end portion. According to this detailed design, when the removeable coupler is engaged to the second delivery member's proximal end portion the inflation lumen is adapted to fluidly couple to a pressurizeable fluid source. In an alternative mode of operation, by removing the removeable coupler from the second delivery member's proximal end portion the second delivery member is adapted to be backloaded through the lumen of the first delivery member.

In another aspect of the endolumenal prosthesis delivery assembly mode of the invention, the endolumenal prosthesis includes an endolumenal stent which forms a stent passageway. The stent is adjustable from a radially collapsed condition with a collapsed outer diameter to a radially expanded condition with an expanded outer diameter. The expanded outer diameter is larger than the collapsed outer diameter and is also adapted to radially engage the body lumen wall. Further to this aspect, the prosthesis coupler includes an expansion member which is adapted to adjust the endolumenal stent from the radially collapsed condition to the radially expanded condition.

In one variation of the endolumenal prosthesis aspect of the assembly, the stent is a balloon expandable stent. According to this variation, the expansion member includes an expandable member which is engaged within the stent passageway and is radially expandable. The radially expandable member is adapted to force the endolumenal stent from the radially collapsed condition to the radially expanded condition.

In another variation of the endolumenal prosthesis aspect of the assembly, the endolumenal stent is a self-expanding stent. According to this stent variation, the expansion member includes a delivery sheath with an inner diameter which approximates the collapsed outer diameter of the endolumenal stent. The sheath is adjustable from a confining position to a releasing position. With the sheath in the confining position, the stent is in the radially collapsed condition and is coaxially contained and compressed against an outward radial bias within the delivery sheath. Alternatively, with the sheath in the releasing position, the stent is released from within the delivery sheath and is allowed to thereby expand to the radially expanded condition. In a further aspect, of this embodiment, the distal end of the second delivery member is anchored just distal of the lumenal site desired for stent placement. The stent assembly is then tracked over the second delivery member until its distal end abuts the anchor of the second delivery member. The sheath is then withdrawn, while pressure is exerted on the stent via an inner member, keeping it in abutting relationship with the anchor.

In still a further variation of the endolumenal prosthesis aspect of the assembly, a graft member is engaged to the endolumenal stent to form a stent-graft prosthesis which is adapted to couple to the first delivery member.

In another aspect of the endolumenal prosthesis delivery assembly mode of the invention, the anchor includes a suction port which is coupled to a suction lumen extending along the second delivery member. The suction lumen is adapted to fluidly couple the suction port to a vacuum source such that the anchor is adapted to be secured to the body lumen wall with suction from the source which is applied at the suction port.

Another mode of the present invention is a method for delivering an endolumenal prosthesis to a desired location within a body lumen that is formed at least in part by a body lumen wall in a mammalian body. This method includes slideably engaging the distal end portion of a first delivery member, which includes a prosthesis coupler removeably engaged with an endolumenal prosthesis, with the distal end portion of a second delivery member. The distal end portion of the second delivery member is positioned within the body lumen and is anchored within the body lumen at an anchoring location that is distal to the desired location. After anchoring the second delivery member's distal end portion, the first delivery member is slideably advanced along the first delivery member until the endolumenal prosthesis is positioned within the body lumen at the desired location.

In one aspect of the method mode of the invention, the body lumen has a severe bend and the desired location is located along the body lumen distally of the severe bend. In another variation of this aspect the body lumen has two successive bend regions, and the anchoring location is located along the body lumen distally of the two successive bend regions. In still another variation of this aspect, the desired location is located along a side branch lumen extending distally from a bifurcation.

In another aspect of the method mode of the invention, the distal end portion of the second delivery member is anchored at the anchoring location by expanding an expandable member along that distal end portion from a radially collapsed condition to a radially expanded condition which radially engages the body lumen wall at the anchoring location.

In another aspect of the method mode of the invention, the distal end portion of the second delivery member is anchored at the anchoring location by applying suction to the body lumen wall at the anchoring location through a distal suction port located along the second delivery member's distal end portion distally of the endolumenal prosthesis.

In another aspect of the method mode of the invention, after securing the anchor at the anchoring location and before tracking the distal end portion of the first delivery member over the distal end portion of the second delivery member, the second delivery member's proximal end portion is pulled by a user to impart tension on the respective distal end portion. According to this tensioning aspect of the method, the second delivery member is stiffened within the anatomy proximally of the anchor and is made taught in order to provide more robust support as a rail over which the first delivery member may track to the desired location. In yet a further aspect, the supportive rail formed by anchoring and tensioning the second delivery member prevents guide catheter back-out as the first delivery member is tracked over the second delivery member to the desired location.

In another initial guidewire tracking aspect of the method mode of the invention, the first delivery member is initially coupled to and tracked over an initial guidewire positioned within the body lumen before slideably engaging the distal end portion of the first delivery member with the distal end portion of the second delivery member and before anchoring the second delivery member's distal end portion at the anchoring location. According to this aspect, the first delivery member is able to track distally over the initial guidewire only until the endolumenal prosthesis is positioned within the body proximally of the desired location. After the unsuccessful attempt to advance the prosthesis into the desired location over the initial guidewire, the guidewire is withdrawn from the body lumen and removed from the body. After withdrawing the initial guidewire from the body, the first delivery member is slideably engaged to the second delivery member and the second delivery member is positioned within the body lumen and anchored at the anchoring location.

In one variation of this initial guidewire tracking aspect of the method mode of the invention, the endolumenal prosthesis is able to be positioned within the body only proximally of the desired location because, while the first delivery member is advanced over the initial guidewire, the initial guidewire is prolapsed at least partially out of the body lumen. As stated above, after the unsuccessful attempt to advance the prosthesis into the desired location over the initial guidewire, the guidewire is withdrawn from the body lumen and removed from the body. After withdrawing the initial guidewire from the body, the first delivery member is slideably engaged to the second delivery member and the second delivery member is positioned within the body lumen and anchored at the anchoring location.

In another variation of the initial guidewire tracking aspect, the body lumen is a side branch which extends distally from a bifurcation region of a body lumen, the bifurcation region further comprising a second branch lumen and a bifurcation. According to this variation the initial guidewire is prolapsed out of the side branch lumen while the distal end portion of the first delivery member advances distally within the second branch lumen, rather than tracking over the initial guidewire into the side branch and to the desired location. Again, after the unsuccessful attempt to advance the prosthesis into the desired location over the initial guidewire, the guidewire is withdrawn from the body lumen and removed from the body. After withdrawing the initial guidewire from the body, the first delivery member is slideably engaged to the second delivery member and the second delivery member is positioned within the body lumen and anchored at the anchoring location.

In still another bifurcation variation for the initial guidewire tracking aspect of the method mode of the invention, prior to withdrawing and removing the initial guidewire from the body, the distal end portion of the first delivery member is confronted against the bifurcation while the first delivery member is advanced distally over the initial guidewire positioned within the side branch. Again, after the unsuccessful attempt to advance the prosthesis into the desired location over the initial guidewire, the guidewire is withdrawn from the body lumen and removed from the body. After withdrawing the initial guidewire from the body, the first delivery member is slideably engaged to the second delivery member and the second delivery member is positioned within the body lumen and anchored at the anchoring location.

BRIEF DESCRIPTION OF THE DRAWINGS

FIG. 1A shows an exploded perspective view of the various components of one endolumenal prosthesis delivery assembly according to the present invention, which assembly is shown to include an endolumenal prosthesis, a first delivery member with a prosthesis coupler, a second delivery member with an anchor, and first and second actuators adapted to engage the first and second delivery members, respectively, and to couple to the prosthesis coupler and anchor, also respectively.

FIG. 1B shows a perspective view of the endolumenal prosthesis delivery assembly shown in FIG. 1A, although showing the various prosthesis, delivery member, and actuator components as they are respectively engaged in a completed assembly.

FIG. 2A shows a partially longitudinally cross-sectioned perspective view of one delivery member with an anchor which is particularly adapted for use as the second delivery member according to the endolumenal prosthesis delivery assembly shown in FIGS. 1A–B.

FIG. 2B shows a transverse cross-sectional view taken along line 2B—2B through the elongate body of the delivery member shown in FIG. 2A.

FIG. 3A shows a partially cross-sectioned, longitudinal perspective view of another delivery member with an anchor which is also particularly adapted for use as the second delivery member according to the endolumenal prosthesis delivery assembly shown in FIGS. 1A–B.

FIG. 3B shows a transverse cross-sectional view of one particular construction for the distal end portion of a tubular member which is adapted for use according to the delivery member shown in FIG. 3A.

FIG. 5A shows one operational mode of a percutaneous translumenal method according to the present invention, and shows a perspective view of a guidewire after its distal end portion is positioned along a region of stenosis along a first side-branch vessel that extends distally beyond a bifurcation region.

FIG. 5B shows another sequential operational mode of the percutaneous translumenal method shown in-part in FIG. 5A, and shows a perspective view of a balloon angioplasty catheter after it is tracked over the guidewire such that an expandable balloon on the balloon catheter's distal end portion is positioned at the stenosis and is expanded to dilate the stenosis.

FIG. 5C shows still another sequential operational mode of the percutaneous translumenal method shown in-part in FIGS. 5A–B, and shows a perspective view of a first delivery member releasably coupled to an endolumenal prosthesis in a first position, which is characterized by a radially collapsed condition, and further showing the first delivery member after prolapsing the guidewire out of the first side-branch vessel and into the bifurcation region toward a second side-branch vessel in a failed attempt to track the first delivery member over the guidewire and into the first side-branch vessel.

FIG. 5D shows yet another sequential operational mode of the method shown in part in FIGS. 5A–C, and shows a perspective view of the first delivery member, including the endolumenal prosthesis in the first position, after it is slideably engaged to a second delivery member that includes an anchor which is secured at an anchoring location along the first side-branch vessel distally of the stenosis.

FIG. 5E shows still another sequential operational mode of the method shown in part in FIGS. 5A–D, and shows a perspective view of the endolumenal prosthesis delivery assembly shown in FIG. 5D after tracking the first delivery member over the second delivery member such that the endolumenal prosthesis is positioned along the stenosis region of the first side-branch vessel.

FIG. 5F shows another sequential operational mode of the method shown in-part in FIGS. 5A–E, and shows a perspective view of the endolumenal prosthesis delivery assembly shown in FIGS. 5D–E after expanding an expandable member which forms the prosthesis coupler to thereby adjust the endolumenal prosthesis from the first position to a second position, which is characterized by a radially expanded condition that is adapted to engage the vessel wall along the stenosis region.

FIG. 6A shows a perspective view of a guiding catheter backing out of a right coronary ostium while advancing a first delivery catheter with an endolumenal prosthesis over a conventional guidewire and against a tight stenosis.

DETAILED DESCRIPTION OF THE INVENTION

Figure 4A:
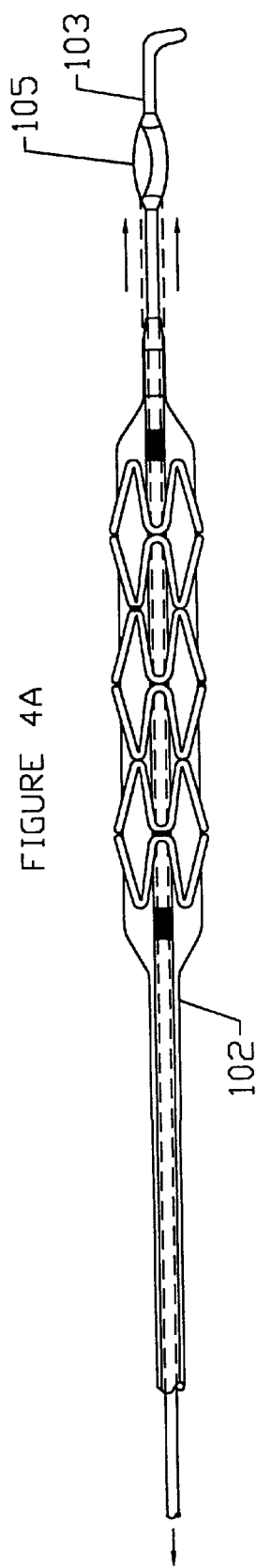
FIG. 4A shows a schematic view of a first delivery member, which is coupled to an endolumenal prosthesis, and a second delivery member which is back-loaded into the first delivery member and includes one type of anchor.

One endolumenal prosthesis delivery assembly (1) according to the present invention is shown in FIG. 1B and includes a first delivery member (2), a second delivery member (3), and an endolumenal prosthesis (4).

Particularly in reference to endolumenal prosthesis (4), the variation according to FIG. 1A provides this prosthesis as a "balloon-expandable" type of endolumenal stent. In more detail, endolumenal prosthesis (4) includes a plurality of connected elements forming an interior prosthesis passageway. Furthermore, endolumenal prosthesis (4) is adjustable under outward radial force from a first position, which is characterized by a radially collapsed condition that is adapted to be delivered to a desired location along a body lumen, to a second position, which is characterized by a radially expanded condition that is adapted to engage the body lumen's wall for implantation there.

Various known stent embodiments may be suitable substitutes for the endolumenal prosthesis in the overall assembly of the present invention. For example, various known balloon expandable stents may be suitable substitutes according to the assembly of the invention, in addition to various self-expanding stents, so long as such assemblies may track over a delivery member with an anchor as described herein by reference to the embodiments. Moreover, while a stent is therefore generally shown and described herein by reference to the preferred embodiments, it is further contemplated that other endolumenal prostheses such as expandable grafts or stent-grafts may also be interchangeably combined in the overall assemblies of the embodiments shown and described without departing from the scope of the present invention.

First delivery member (2) is shown in FIG. 1A as a balloon catheter and includes an elongate body or shaft (20), having a proximal end portion (21) and a distal end portion (23). Distal end portion (23) includes a balloon (25) which is fluidly coupled to a proximal coupler (22) via an inflation lumen (not shown) that extends between proximal coupler (22) and balloon (25) along shaft (20). Proximal coupler (22) is adapted to fluidly couple balloon (25) to an actuator (6) which is a pressurizeable fluid source in order to inflate balloon (25) under applied fluid pressure and thereby adjust balloon (25) from a radially collapsed condition (26) to a radially expanded condition (27) (shown in shadow in FIGS. 1A–B). The pressurizeable fluid source may include for example a liquid, such as a radiopaque solution, or a gas for inflating the balloon (25). Balloon (25) in the radially collapsed condition (26) has a collapsed outer diameter od and in the radially expanded condition (27) has an expanded outer diameter OD which is larger than the collapsed outer diameter od.

Second delivery member (3) is shown in FIG. 1A to include an elongate member (30) with a proximal end portion (31) and a distal end portion (33). Distal end portion (33) further includes an anchor (35) which is shown as an expandable balloon that is fluidly coupled via an inflation lumen (not shown) to proximal coupler (32), also shown in FIG. 1A. Proximal coupler (32) is further adapted to couple to actuator (5) which is a pressurizeable fluid source that is adapted to inflate the balloon forming anchor (35). According to this balloon aspect of the specific embodiment of FIG. 1A, anchor (35) is thereby adjustable with the pressurizeable fluid source from a first position, which is characterized by a radially collapsed condition (36) with a collapsed outer diameter d, to a second position, which is characterized by a radially expanded condition (37) with an expanded outer diameter D that is larger than collapsed outer diameter d.

Distal end portion (33) of second delivery member (3) is also shown in the FIG. 1A embodiment to include a shaped distal tip (34) which is located distally of anchor (35). The overall construction for second delivery member is adapted such that shaped distal tip (34) is steerable by torquing proximal end portion (31). In addition, shaped distal tip (34) is constructed of radiopaque materials which are visible under X-ray or fluoroscopic observation. According to this overall construction, second delivery member (3) is adapted to function as a "guidewire", which term is herein intended to mean an elongate delivery member which is adapted to controllably subselect and be positioned within a desired, remote in vivo body lumen via percutaneous translumenal control, and also to provide a rail which is adapted to be coaxially engaged within another device and over which the other device may track into that body lumen.

The various components shown in FIG. 1A are further described in their respectively coupled relationships in a completed assembly by further reference to FIG. 1B. In more detail to the overall assembly shown in FIG. 1B, endolumenal prosthesis (4) is provided in its respective first position while removeably engaged over balloon (25) of first delivery member (2). In addition, first delivery member (2) is shown slideably engaged with second delivery member (3). Further to the first and second delivery member coupling according to the embodiment of FIG. 1B, second delivery member (3) is slideably engaged within a lumen or passageway (not shown) extending within first delivery member (2) between a distal port (29) and a proximal port (28). Anchor (35) is also shown in FIG. 1B extending distally from distal port (29), while proximal end portion (31) of second delivery member (3) is shown extending proximally from proximal port (28).

Further to the operational modes of the overall assembly shown and described by reference to FIG. 1B, endolumenal prosthesis (4) is adapted to be delivered within a desired region of a body lumen in the first position (the position shown for the prosthesis in FIGS. 1A–B) by use of first and second delivery members (2,3). Endolumenal prosthesis is thereafter adapted to be implanted within that desired region by expanding balloon (25) on first delivery member (2) to its radially expanded condition (27), thereby expanding and adjusting the endolumenal prosthesis (4) from the first position to the second position. Further more detailed description of the sequential modes of operation for delivering and implanting endolumenal prosthesis (4) with first and second delivery members (2,3) will be described in more detail below.

According to the overall endolumenal prosthesis delivery assembly of the invention just described by reference to FIGS. 1A–B, one specific design which is believed to be suitable as the second delivery member is shown in FIGS. 2A–B.

FIG. 2A shows second delivery member (3) to include an elongate body (60) with proximal end portion (61) and distal end portion (63). Distal end portion (63) includes an anchor which is a balloon (65) and also includes a distal tip (70) located distally of the balloon (65).

Elongate body (60) is further shown to include a tubular member (60'), shown in cross-section in FIG. 2B, which extends along the proximal end portion (61) and terminates distally of balloon (65). Tubular member (60') forms an inflation lumen (60")(shown in FIG. 2B) which extends between a proximal port (68) and a distal port (64) located beneath the balloon (65). Inflation lumen (60") terminates distally of the balloon (65) where it is engaged in a fluid tight seal to a core wire (74) that forms in part distal tip (70).

Tubular member (60') is torsionally coupled to distal tip (70) and therefore preferably is a relatively stiff member, at least in the most proximal extremity. In one construction which is believed to be suitable according to this embodiment, tubular member (60') is constructed of a metal hypotube. In a more detailed construction, such a metal hypotube may be made of a superelastic metal, such as for example an alloy of nickel and titanium, or of another metal such as stainless steel. In still a further alternative construction, a stiff polymeric tube may be suitable, such as for example a polyimide tube. Still further, a composite construction such as a wire coil or braid impregnated polymeric tube may be suitable.

Further to the torsional coupling to the more proximally disposed tubular member just described, distal tip (70) is further shown in FIG. 2A to be shapeable to form a shaped tip (78) as opposed to merely being shaped as shown previously in the more schematic illustration of FIGS. 1A–B. Distal tip (70) includes core wire (74) that is engaged to and secured within tubular member (60') in a fixed arrangement, such as for example by soldering, welding, swaging, or by use of adhesives. In addition, this core wire is shown to include a taper from a proximal section (74) to a reduced diameter distal section (74'). A radiopaque coil (76) is shown in longitudinal cross section in FIG. 2A and is disposed over the distal section (74'). Coil (76) is secured to core wire (74) at the distal terminus of the device and may be secured to the core wire according to known methods such as by soldering, welding, or adhesives. Moreover, the shapeability of distal tip (70) may be achieved according to well known aspects of conventional shapeable guidewire designs.

A proximal coupler (62) is also shown in FIG. 2A and is adapted to removeably engage proximal end portion (61) in order to fluidly couple to the balloon (65) and also to couple to an expansion actuator (69) which is a pressurizeable fluid source. In the particular embodiment shown in FIG. 2A, proximal coupler (62) is removeably engageable with proximal end portion (61) by threaded coupling between those components. Further to this removeable feature for proximal coupler (62), by uncoupling the proximal coupler (62) the proximal end portion (61) is adapted to be "backloaded" into the tracking lumen provided on the first delivery member in order to achieve a coupled arrangement such as is shown between delivery members in FIG. 1B.

Balloon (65) is shown in FIG. 2A to be sealed at each of its proximal and distal ends to the elongate body and on either side of the distal port (64). These seals may be achieved by use of an adhesive, according to a variation requiring sealing a polymeric balloon to a metallic tubular member, or by use of solvent or heat/melt bonding according to variations which combine a polymeric balloon with a tubular member having at least a polymeric outer surface in the region of the balloon seals.

Balloon (65) is also shown in FIG. 2A to form an elastic tubular member that is adapted to stretch and therefore radially expand under fluid pressure applied through distal port (64). In one beneficial construction, balloon (65) is constructed of a highly elastic material, such as for example polyurethane, latex, silicone, or compounds or combinations of these materials. In one elastic construction which is believed to be beneficial, the balloon preferably exhibits at least about two hundred (200%) percent elastic expansion (or expanding in diameter to three times the initial diameter) under an applied pressure of about three to five atmospheres. It is believed that such elastic properties for a balloon anchor may provide several benefits according to the overall assembly of the invention.

In one aspect of this elastic mode of construction, a low profile may be achieved in order to slideably engage the balloon anchor within the tracking lumen of a first delivery member, such as according to a slideably coupled assembly as shown in FIG. 1B. For example, in one contemplated variation the first delivery member coupled to the prosthesis has a tracking lumen inner diameter that is adapted generally to track over guidewires having an outer diameter of about 0.018 inches, wherein the lumen inner diameter is may be from about 0.020 to about 0.025 inches, and usually about 0.023 inches. According to this variation, the outer profile for the balloon anchor is preferably less than these lumen inner diameters for applications where advancing the balloon anchor within and through the inner lumen in a "front-loading" method is desirable.

Furthermore, a significant increase in diameter may be required to the second position or radially expanded condition in order to engage the lumenal wall to effectively anchor at the anchoring location. It is believed that general use of the balloon anchor aspect of the present invention may require balloon inflations sufficient to engage vessels having an inner diameter of about 2 millimeters, or 0.079 inches, nearly four times expansion of a 0.020 profile balloon in the radially collapsed condition. According to the elastic variation for the balloon anchor construction, this significant range in sizing from the first to the second positions may also achievable due to the highly compliant nature of the material under pressure.

Still further, the intended site for inflating and securing the balloon anchor within a vessel is generally in an anchoring region which is distal to the desired site for prosthesis implantation. It is believed that low pressure inflations concomitant with the elastic variation may also be beneficial in such anchoring regions since such regions may present normal healthy tissue outside the region of wall irregularity that is requiring the prosthesis.

Notwithstanding the benefits just described for a compliant balloon variation for an anchor according to the present invention, it is further contemplated that other balloon materials may also be suitable in some circumstances. For example, a balloon formed of a material such as polyethylene, polyolefin copolymer, polyvinylchloride, polyamide, polyethelyneterepthalate, or the like may also be suitable in some circumstances. According to these less compliant materials, such balloons would be provided in a folded state when in the first position or radially collapsed condition. In one aspect, however, in order to achieve the requisite outer diameter in the second position or radially expanded condition in order to engage a vessel wall for anchoring, such balloons may have an outer profile that is not conducive to slideable engagement within the tracking lumen of a first delivery member carrying the endolumenal prosthesis according to the assembly of the invention. Therefore, it is believed that such variations may be more amenable to including the removeable proximal coupler embodiment in order to accommodate backloading of the second delivery member into the first delivery member.

Another design which is believed to be suitable as the second delivery member is shown in FIGS. 3A–B.

FIG. 3A shows second delivery member (8) to include an elongate body (80) with proximal end portion (81) and distal end portion (83). Distal end portion (83) includes an anchor which is a balloon (85) and also includes a distal tip (90) located distally of the balloon (85).

Elongate body (80) is further shown to include a tubular member (80'), shown in cross-section in FIG. 2B, which includes a metallic hypotube, such as previously described by reference to FIG. 2A, extending along the proximal end portion (81) and a polymeric tubing secured to the hypotube and extending distally therefrom along distal end portion (83) and terminating distally of balloon (85). Tubular member (80') forms an inflation lumen (80") which extends between a proximal port (88) and a distal port (84) located beneath the balloon (85). Inflation lumen (80") terminates distally of balloon (85) where it is engaged in a fluid tight seal (97) to a core wire (94) that forms in part distal tip (90).

As further shown in FIG. 3A, distal tip (90) includes core wire (94) that is engaged within and extends distally from tubular member (80'). Core wire (94) is secured to tubular member (80') in a proximal region of the assembly, such as for example by soldering, welding, swaging, or by use of adhesives, or, as is shown in FIG. 3A for the purpose of further illustration at crimp joint (99). In addition, this core wire (94) is shown to include a taper from its proximal section to a reduced diameter distal section (94'), and may have several tapered regions such as is shown in various segments of core wire (94) in FIGS. 3A–B. A radiopaque coil (96) is shown in longitudinal cross section in FIG. 3A and is disposed over the distal section (94'). Coil (96) is secured at each ends to core wire (94) at the distal terminus of the device and may be secured as such according to the various methods previously described above. In the particular embodiment of FIG. 3A, coil (96) is secured at its proximal end to both the core (94) and also the distal end of tubular member (80') in a manner which plugs the distal end of the tubular member (80') in a fluid tight seal (97) such that inflation lumen (80") is isolated from leakage during inflation. Further to distal tip (90) according to the FIG. 3A embodiment, the tip may also be shaped or shapeable in order to facilitate use of the delivery member as a guidewire.

A proximal coupler (100) is also shown in shadow in FIG. 3A and is adapted to removeably engage proximal end portion (81) in order to fluidly couple to the balloon (85) and also to couple to an expansion actuator (not shown) which is a pressurizeable fluid source. As previously described by reference to the FIG. 2A embodiment, the proximal coupler may be removeably engageable with proximal end portion (81), such as by a threaded coupling between those components, in order to accommodate a "backloaded" configuration.

Balloon (85) is also shown in FIG. 3A to be sealed at each of its proximal and distal ends (86) to the elongate body and on either side of the distal ports (84), and may have a material construction and be sealed to the tubular member for example according to the various alternative modes previously described above. Further to distal ports (84), a coiled or braided construction may be provided as a part of tubular member (80') such that the distal inflation ports are formed between spacings between support members of the coil or braid, such as is shown in FIG. 3B by arrows through spacings between struts of coil (84').

Figure 4B:
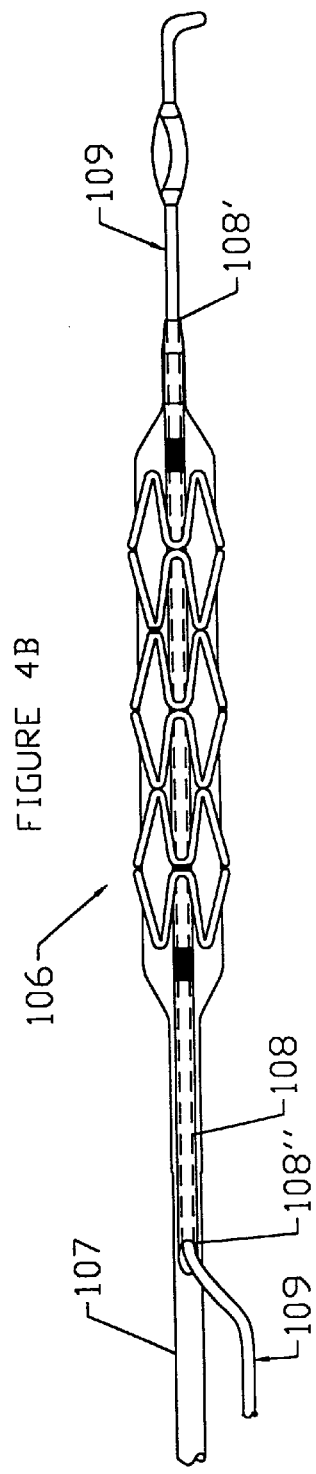
FIG. 4B shows a similar schematic view of an endolumenal prosthesis assembly as that shown in FIG. 4A, although showing the second delivery member back-loaded into a tracking lumen which extends only along the distal end portion of the first delivery member.
Figure 4C:
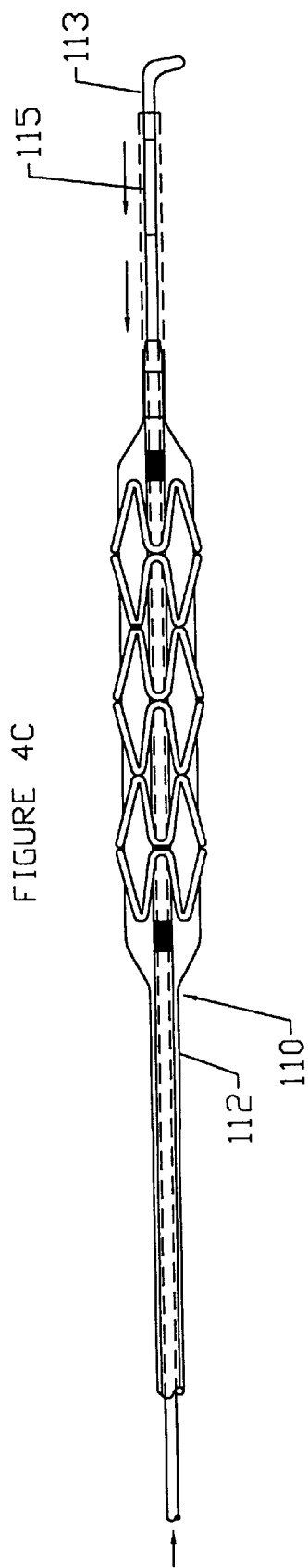
FIG. 4C shows another similar schematic view of an endolumenal prosthesis assembly as that shown in FIG. 4A, although showing the second delivery member to include an anchor which is adapted to slideably engage a tracking lumen extending through the first delivery member in order to accommodate a frontloaded coupling between the delivery members.

For the purpose of further illustrating the alternative "backloading" and "frontloading" coupling between the first and second delivery members as previously described according to the present invention, various alternative assemblies which embody various coupling arrangements between the delivery members are shown in FIGS. 4A–C.

FIG. 4A shows a schematic view of a back-loaded coupling between a first delivery member (102) and a second delivery member (103) wherein the anchor is a folded balloon (105) having an outer profile that is larger than the inner diameter of the tracking lumen of the first delivery member (102). According to this variation, first delivery member (102) is shown in shadow as its position is advanced relative to the second delivery member (103). More particularly, second delivery member (103) is backloaded through the first delivery member (102) until the first delivery member abuts against the folded balloon (105).

The backloaded coupling arrangement shown in FIG. 4A is shown in a further variation in FIG. 4B, wherein an alternative endolumenal prosthesis delivery assembly (106) is shown to include a first delivery member (107) which has a tracking lumen (108)(shown in shadow) that extends between distal and proximal ports (108',108") which are both located along a distal end portion of first delivery member (107). As shown in FIG. 4B, second delivery member (109) slideably engages the tracking lumen (108) and extends proximally from proximal port (108") along side first delivery member (107). It is believed that the lumenal structure for the first delivery member (107) shown in FIG. 4B is advantageous in a backloading method of coupling to the second delivery member (109) due to the shortened lumen (108) which allows for the slideable engagement for the respective delivery members to be achieved entirely outside of a delivery sheath.

Still a further coupling arrangement for an endolumenal prosthesis delivery assembly is shown at assembly (110) in FIG. 4C, wherein the balloon anchor on the second delivery member (113) is an elastic tubular balloon (115) as previously described. Further to this variation, first delivery member (112) is shown in shadow as it is advanced over the elastic tubular balloon (115) without significant obstruction in order to illustrate the ability to slideably engage a low profile balloon anchor, such as of the elastic type, within the first delivery member (112).

FIGS. 5A–F show an endolumenal prosthesis delivery assembly according to the present invention during sequential modes of use in positioning and implanting an endolumenal prosthesis in a side branch lumen (153) distally beyond a bifurcation region (152) of a body lumen (150).

In one particular mode of the present invention, the endolumenal prosthesis is implanted within the desired location subsequent to a recanalization procedure formed upon a stenosis (154) at the desired location. Therefore, in an exemplary embodiment of this aspect, FIGS. 5A–B sequentially show positioning a conventional guidewire (170) within the side-branch lumen (153) extending from a bifurcation (152) such that the guidewire is placed through and beyond stenosis (154), and then tracking a balloon angioplasty catheter (180) over the wire (170) and dilating the stenosis (154) with balloon (185).

FIG. 5C further illustrates a subsequent attempt to advance a stent delivery assembly (200) over the same guidewire (170) after removing the angioplasty catheter. As is demonstrated by this Figure, the first delivery member (202) tends to advance in a straight path along the main lumen (151) rather than follow the guidewire (170). First delivery member (202) therefore prolapses guidewire (170) outwardly of side-branch lumen (153) in a failed attempt to position the stent prosthesis (204) at the desired site of the original stenosis (154).

FIG. 5D therefore initially illustrates the use of the endolumenal prosthesis delivery assembly (200) according to the present invention in attempt to overcome the stent delivery challenge past a drastic bend at a bifurcation region of a body lumen. According to the sequential mode shown in FIG. 5D, the initial guidewire has been removed and replaced with a second delivery member (203) that includes a shaped and steerable tip (234) and also an anchor (235) which is an expandable balloon as previously described by reference to the embodiments above. Anchor (235) is further shown in an expanded condition which is radially engaged and secured within the side-branch lumen (153) at an anchoring location (156) distally of the desired stenting site of the dilated lesion (154).

As is shown by way of an illustrative arrow in FIG. 5D and subsequently in FIG. 5E, first delivery member (202) is able to advance over second delivery member (203) and into the side branch lumen (153) such that endolumenal prosthesis (204) is positioned at the desired location (154) for implantation. This is because the anchor (235) prevents prolapsing of the second delivery member (203) proximally out of the side-branch lumen (153) while first delivery member (202) is advanced along the main lumen (151) and into the bifurcation region (152). Moreover, as further shown in a proximally pointing arrow in FIG. 5D, tension may be placed upon second delivery member (203) by pulling on its proximal end portion (not shown) while the anchor is secured at the anchoring location. This tension effectively stiffens the second delivery member (203) and enhances its function as a support member during the tracking mode of operation for the overall delivery assembly.

FIG. 5F further shows endolumenal prosthesis (204) after being adjusted to the second position in the radially expanded condition by the balloon coupler on the first delivery member, thereby implanting the prosthesis at the lesion site (154). While not shown, the various components of the assembly may be subsequently removed after deflating the corresponding expanded members, such as the balloon releasably engaged within the endolumenal prosthesis and also such as the anchor, which are otherwise engaged to the lumenal wall.

Use of an endolumenal prosthesis delivery assembly according to the present invention are shown in a clinical setting during various modes of operation in FIGS. 6A–8.

One mode of operation for endolumenal prosthesis delivery assembly (200) is shown in FIG. 6A. According to this mode, an endolumenal prosthesis (201) is engaged to a first delivery member (210) which is slideably engaged over a guidewire (220) positioned distally of serial lesions along an artery (250), which is shown in the particular mode in FIG. 6A as a right coronary artery. This coupled assembly is shown delivered into artery (250) through guide catheter (230). As is shown illustratively by way of arrows in FIG. 6A, guide catheter (230) disengages ostium (252) of artery (250) while endolumenal prosthesis (201) is advanced against a tight lesion (254) over guidewire (220), thereby resulting in "guide catheter back-out" as previously observed and described above according to use of conventional endolumenal prosthesis delivery assemblies.

Figure 6B:
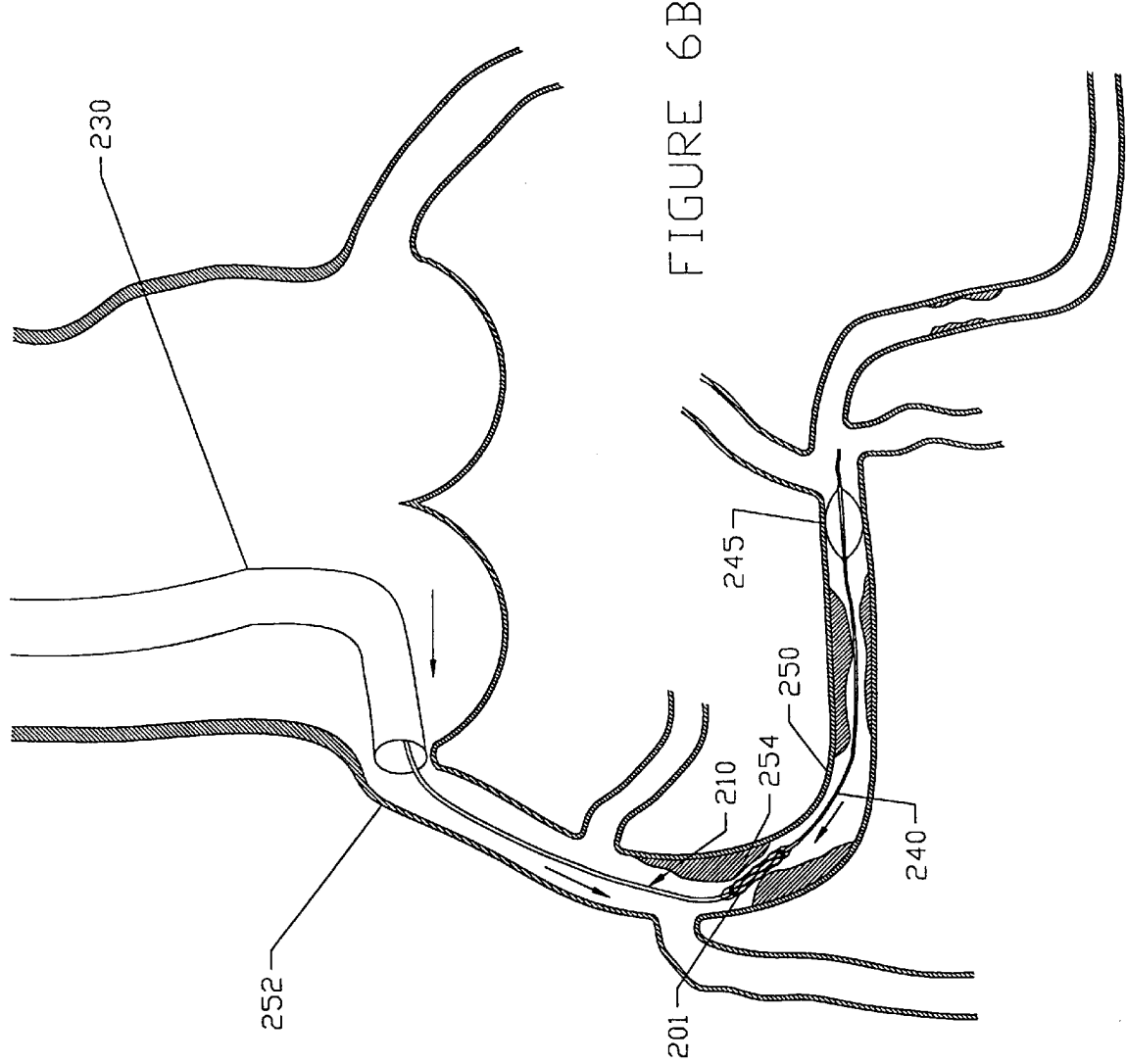
FIG. 6B shows a similar perspective view of an endolumenal prosthesis delivery assembly as that shown in FIG. 6A, although showing the guiding catheter remaining seated within the ostium while advancing the first delivery member and endolumenal prosthesis over a second delivery member while tension is applied to the second delivery member after anchoring it within the lumen distally of the stenosis.

FIG. 6B shows first delivery member (210) engaged over a second delivery member (240) in an assembly according to the various embodiments of the invention previously described, and may be used according to the FIG. 6B view either subsequent to guide catheter back-out according to the mode of use shown in FIG. 6A, or in anticipation and prevention of such a phenomenon as a stand-alone method. Further to the method embodied in FIG. 6B, second delivery member (240) is advanced within artery (250) such that an anchor (245) on second delivery member (240) is positioned within and secured to the lumen at a position beyond the tight lesion (254). As shown illustratively by way of arrows in FIG. 6B, tension is placed upon second delivery member (240) and while the anchor (245) is secured to the artery lumen. With the second delivery member (240) effectively stiffened as such, first delivery member (210) tracks over second delivery member (240) such that prosthesis (201) advances across lesion (254) while the guide catheter (230) remains seated in ostium (252).

Figure 7:
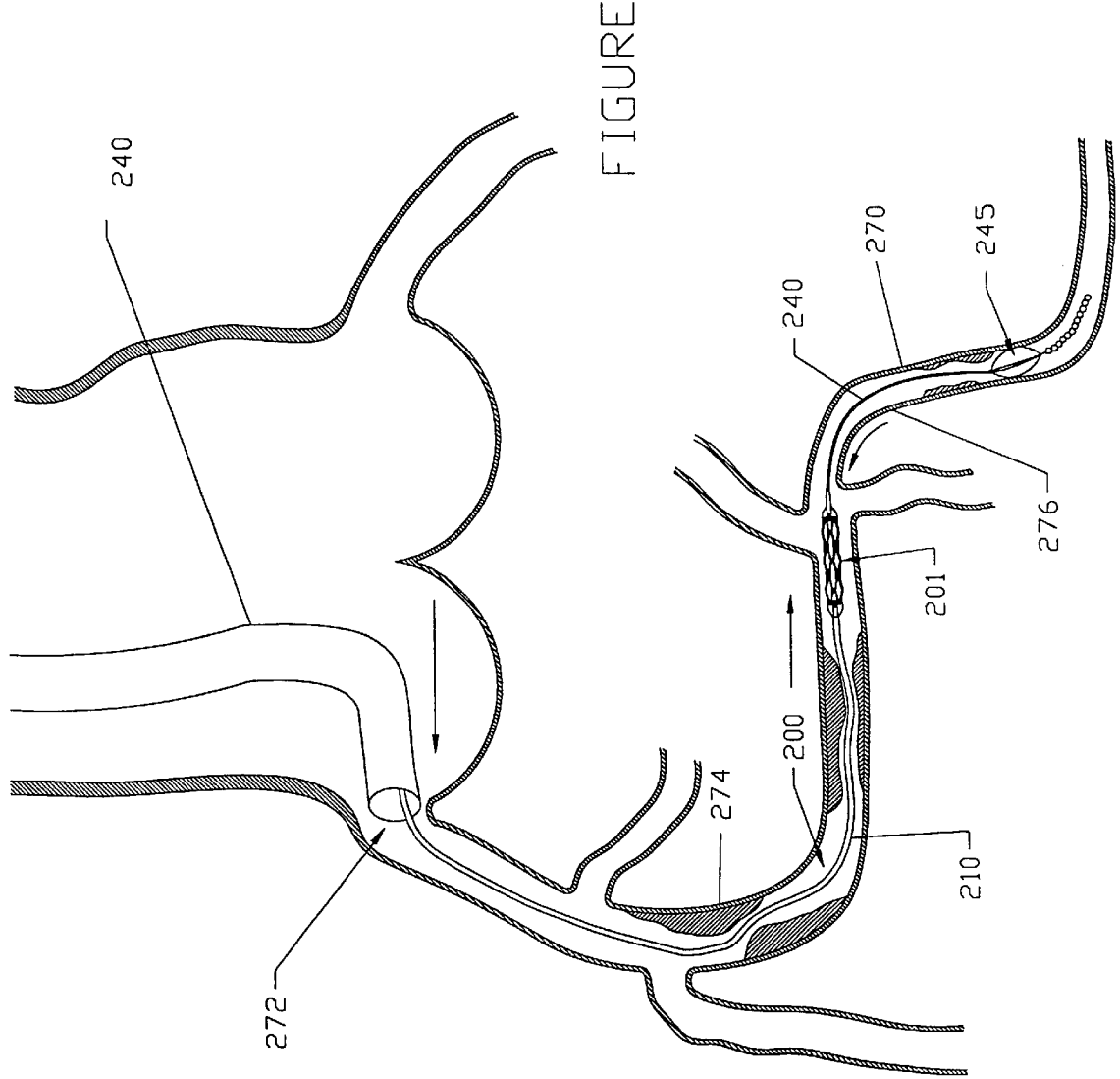
FIG. 7 shows another perspective view of the endolumenal prosthesis delivery assembly shown in FIG. 6B, although showing the guiding catheter remaining seated within an ostium while tracking the first delivery member and endolumenal prosthesis through sequential, tortuous bends over a second delivery member, and while applying tension to the second delivery member after anchoring it to the lumen distally of the bends.

The second delivery member (240) may also be useful according to its anchoring and tensioning modes to allow increased support for tracking the first delivery member (210) and endolumenal prosthesis (201) through sequential, tortuous bends, as is shown in FIG. 7. According to the mode of use for assembly (200) shown in FIG. 7, anchor (245) is positioned within and anchored within artery (270) at a location distally beyond sequential, tortuous bends (274, 276), respectively. Again by advancing the first delivery member (210) and prosthesis (201) over the second delivery member (240) while tensioning the anchored second delivery member (240) (shown by arrows), the prosthesis (201) is shown successfully advanced at least beyond bend (274) while the guide catheter (240) remains seated within ostium (272).

Figure 8:
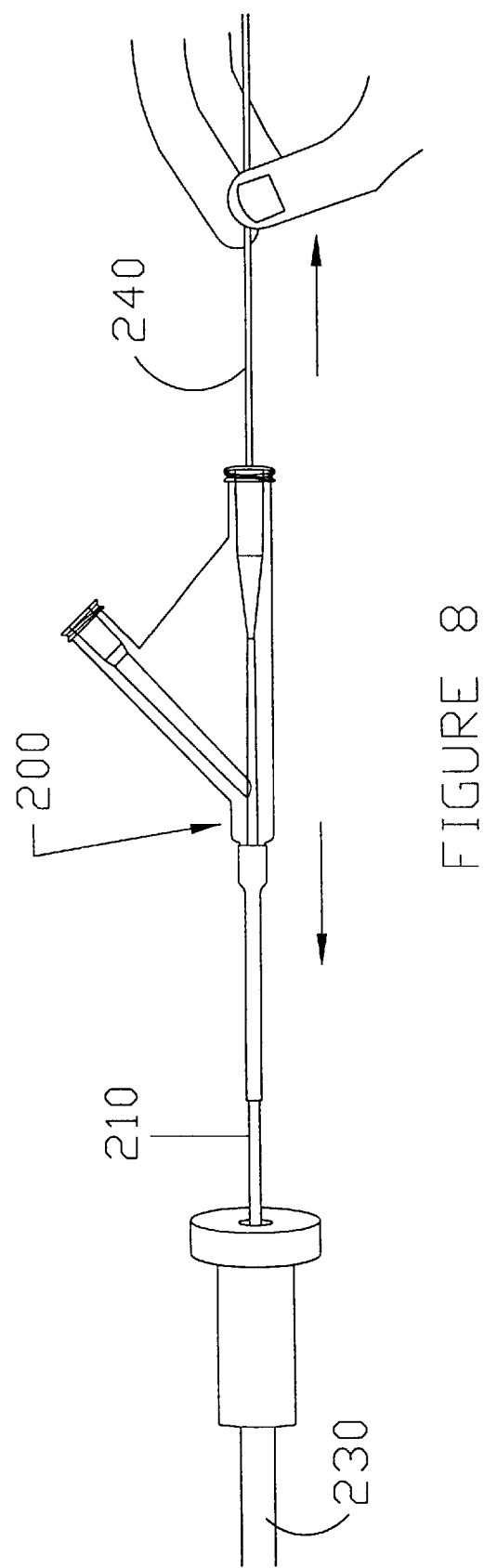
FIG. 8 shows another perspective view of the endolumenal prosthesis delivery assembly shown in FIGS. 6B and 7, although showing only the proximal end portions of the variously engaged components of the assembly wherein the first delivery member is advanced distally within the guiding catheter subsequent to or during application of a proximal tension force on the second delivery member engaged within the first delivery member in order to prevent guide catheter back-out.

For the purpose of further illustration, the proximal components of assembly (200) are shown in FIG. 8 during the tensioning of second delivery member (240) and concomitant advancing of first delivery member (210) thereover and through guide catheter (230).

While particular embodiments have been described in detail above by reference to the Figures, other variations and modifications may be made without departing from the scope of the present invention.

For example, other "anchors" may be provided as suitable substitutes to the expandable balloon variations specifically shown and described. In one more detailed example, expandable cages or mechanical grabbers may suitably engage the vessel lumen wall to secure the delivery member at a predetermined anchoring location during prosthesis delivery. In still a further more detailed example of another "anchor" variation, suction may also be used to secure that delivery member as a secured rail. For instance, a suction port on the distal end portion of a guidewire-type delivery member may be coupled to a vacuum source with sufficient suction force to engage and anchor along a vessel lumen wall.

In addition, other prosthesis couplers and respective first delivery members may also be suitable substitutes for the balloon catheter variations shown and described specifically by reference to the Figures. In one such variation, delivery assemblies and stent couplers of the "self-expanding" type may be modified according to the teachings of the preferred embodiments above and still fall within the scope of the invention. In a more specific embodiment of this variation, the delivery assembly is used to more accurately and reliably position the self-expanding prosthesis. The anchor of the second delivery member is secured just distal of the lesion to be supported. The first delivery member, having the self-expanding prosthesis mounted on the distal end thereof, is advanced over the second delivery member until the self-expanding prosthesis, and its confining sheath abut the anchor. The sheath is then withdrawn while the self-expanding prosthesis is held in abutting relationship with the anchor. As discussed previously, this will minimize, or prevent, the observed tendency of the self-expanding prosthesis advancing or "popping" distally as the sheath is withdrawn.

Moreover, the novel methods described may also be modified without departing from the scope of the invention. In one illustrative variation, the anchor may be secured to a vessel lumen at or proximal to a lesion site where the prosthesis is to be implanted and still be useful in delivering the prosthesis beyond a proximal bifurcation or bend according to the methods previously described above. In another exemplary variation, the method of anchoring a guidewire at an anchoring location, providing tension on the guidewire while it is anchored, and advancing another device over the guidewire and to the desired site while the guidewire is under tension may be performed with other devices than endolumenal prosthesis delivery devices and still fall within the scope of the present invention.

The present invention, as described above by reference to the embodiments as shown in the Figures, includes an endolumenal prosthesis delivery assembly and method of use. Additional modifications to or combinations of the specific assembly embodiments and variations described above which may become apparent to one of ordinary skill from this disclosure, but which have not been specifically described herein, are also contemplated as falling within the scope of the present invention.

What is claimed is:

1. A method for delivering an endolumenal prosthesis to a desired location within a body lumen, comprising the steps of:

positioning a distal end portion of a second delivery member, which includes means on the distal end portion thereof for anchoring the distal end of the second delivery member, at an anchoring location within the body luman that is distal to the desired location;

anchoring the distal end portion of the second delivery member within the body lumen distal to the desired location;

slideably engaging a distal end portion of a first delivery member, which includes a prosthesis coupler engaged to an endolumenal prosthesis, with a proximal portion of the second delivery member;

tracking the first delivery member over the second delivery member until the endolumenal prosthesis is positioned with the body lumen at the desired location; and after anchoring the distal end portion of the second delivery member at the anchoring location and before tracking the first delivery member over the second delivery member, pulling on the proximal end portion of the second delivery member to thereby impart tension to the distal end portion of the second delivery member.

2. The method of claim 1, wherein the endolumenal prosthesis comprises a self-expanding stent having a collapsed outer diameter, and the prosthesis coupler comprises a delivery sheath, confining said self-expanding stent, with an inner diameter which approximates the collapsed outer diameter of the self-expanding stent and which is adjustable from a confining position to a released position, wherein the confining position the endolumenal stent is in the radially collapsed condition and is coaxially contained and compressed against an outward radial bias within the delivery sheath, and wherein the releasing position the endolumenal stent is released from within the delivery sheath and is allowed to thereby expand to the radially expanded condition, and further comprising the steps of:

anchoring the distal end portion of the second delivery member at a location just distal of the desired location;

tracking the first delivery member over the second delivery member such that the self-expanding stent and delivery sheath abut the means for anchoring and span the desired location; and withdrawing the delivery sheath to the releasing position thereby releasing the self-expanding stent and allowing the self-expanding stent to assume a radially expanded condition.

3. A method for preventing a guide catheter from backing out of an ostium of a body lumen while performing a procedure within the body luman, comprising the steps of:

positioning a distal end portion of the guide catheter at the ostium of the body lumen;

positioning a distal end portion of a second delivery member, which includes means on the distal end portion thereof for anchoring the distal end of the second delivery member, at an anchoring location within the body luman that is distal to the desired location;

anchoring the distal end portion of the second delivery member within the body lumen distal to the desired location;

slideably engaging a distal end portion of a first delivery member, which includes a prosthesis coupler engaged to an endolumenal prosthesis, with a proximal portion of the second delivery member;

tracking the first delivery member over the second delivery member until the endolumenal prosthesis is positioned with the body lumen at the desired location; and after anchoring the distal end portion of the second delivery member at the anchoring location and before tracking the first delivery member over the second delivery member, pulling on the proximal end portion of the second delivery member to thereby impart tension to the distal end portion of the second delivery member, thereby preventing the guide catheter from backing out of the ostium of the body lumen while the first delivery member is being tracked over the second delivery member.

* * * * *